(12) United States Patent
Ben-Haim et al.

(10) Patent No.: US 6,447,504 B1
(45) Date of Patent: Sep. 10, 2002

(54) SYSTEM FOR TREATMENT OF HEART TISSUE USING VIABILITY MAP

(75) Inventors: Shlomo Ben-Haim, Haifa; Uri Yaron, Zichron-Yaacov, both of (IL)

(73) Assignee: Biosense, Inc., New Brunswick, NJ (US)

(*) Notice: Subject to any disclaimer, the term of this patent is extended or adjusted under 35 U.S.C. 154(b) by 91 days.

(21) Appl. No.: 09/689,258

(22) Filed: Oct. 12, 2000

Related U.S. Application Data

(63) Continuation of application No. 09/109,820, filed on Jul. 2, 1998, now Pat. No. 6,171,303.

(51) Int. Cl.[7] ............................................. A61B 18/18
(52) U.S. Cl. .......................................... 606/15; 606/10
(58) Field of Search ................................ 606/7, 10, 12, 606/15, 17, 33, 41, 49; 607/89

(56) References Cited

U.S. PATENT DOCUMENTS

| | | |
|---|---|---|
| 4,658,817 A | 4/1987 | Hardy |
| 4,788,975 A | 12/1988 | Shturman et al. |
| 5,125,924 A | 6/1992 | Rudko |
| 5,125,926 A | 6/1992 | Rudko et al. |
| 5,188,111 A | 2/1993 | Yates et al. |
| 5,350,375 A | 9/1994 | Deckelbaum et al. |
| 5,380,316 A | 1/1995 | Aita et al. |
| 5,389,096 A | 2/1995 | Aita et al. |
| 5,391,199 A | 2/1995 | Ben-Haim |
| 5,403,311 A | 4/1995 | Abele et al. |
| 5,403,356 A | 4/1995 | Hill et al. |
| 5,431,168 A | 7/1995 | Webster, Jr. |
| 5,433,198 A | 7/1995 | Desai |
| 5,450,846 A | 9/1995 | Goldreyer |
| 5,487,391 A | 1/1996 | Panescu |
| 5,554,152 A | 9/1996 | Aita et al. |
| 5,566,673 A | 10/1996 | Shiono et al. |
| 5,607,421 A | 3/1997 | Jeevanandam et al. |

(List continued on next page.)

FOREIGN PATENT DOCUMENTS

| | | |
|---|---|---|
| WO | WO 94/06349 A1 | 3/1994 |
| WO | WO 95/07657 A1 | 3/1995 |
| WO | WO 96/05768 A1 | 2/1996 |
| WO | WO 97/24983 A2 | 7/1997 |
| WO | WO 97/25101 A2 | 7/1997 |
| WO | WO 97/29683 A1 | 8/1997 |
| WO | WO 97/29685 A1 | 8/1997 |
| WO | WO 97/29803 A1 | 8/1997 |

OTHER PUBLICATIONS

Mirhoseini et al.; "Transmyocardial Laser Revascularization: A Review"; J. of Clinical Laser Medicine & Surgery vol. 11, No. 1, 1993; pp. 15–19.

Bonn; "High–power lasers help the ischaemic heart"; The Lancet (Science and Medicine) vol. 348, 7/96; p. 118.

Lee et al.; "Effects of laser irradiation delivered by flexible fiberoptic system on the left ventricular internal myocardium"; Brief Communications, vol. 106, No. 3, 9/83 American Heart Journal (from Cardiac Center, Cedars Medical Center; and the University of California at Davis); pp. 587–590.

*Primary Examiner*—Roy D. Gibson
(74) *Attorney, Agent, or Firm*—Louis J. Capezzuto

(57) ABSTRACT

A system for treatment of tissue, such as heart tissue, includes a laser source and a catheter having an optical waveguide which is operatively connected to the laser source. The catheter also includes a position sensor for generating position signals relating to the distal end of the catheter and an electrode for generating signals relating to the viability of the tissue. The system also includes signal processing circuitry for processing the position signals in order to determine position coordinates of the distal end of the catheter as well as the signals relating to the viability of the tissue for determining a viability map of the tissue. The system further includes a display for displaying the viability map.

10 Claims, 9 Drawing Sheets

U.S. PATENT DOCUMENTS

| | | |
|---|---|---|
| 5,651,786 A | 7/1997 | Abela et al. |
| 5,724,975 A | 3/1998 | Negus et al. |
| 5,738,096 A | 4/1998 | Ben-Haim |
| 5,769,843 A | 6/1998 | Abela et al. |
| 5,824,005 A | 10/1998 | Motamedi et al. |
| 5,840,031 A | 11/1998 | Crowley |
| 5,871,495 A | 2/1999 | Mueller |
| 5,885,272 A | 3/1999 | Aita et al. |
| 5,891,133 A | 4/1999 | Murphy-Chutorian |
| 5,893,848 A | 4/1999 | Negus et al. |
| 5,931,934 A * | 8/1999 | Li et al. .................. 360/32 |
| 5,964,757 A | 10/1999 | Ponzi |
| 6,023,638 A | 2/2000 | Swanson |
| 6,024,739 A | 2/2000 | Ponzi et al. |
| 6,027,473 A | 2/2000 | Ponzi |
| 6,063,022 A | 5/2000 | Ben-Haim |
| 6,210,362 B1 * | 4/2001 | Ponzi .................. 604/95.01 |

\* cited by examiner

SYSTEM FOR TREATMENT OF HEART TISSUE USING VIABILITY MAP

CROSS-REFERENCE TO RELATED APPLICATIONS

This application is a continuation of U.S. patent application Ser. No. 09/109,820 filed on Jul. 3, 1998 now U.S. Pat. No. 6,171,303 issued Jan. 9, 2001.

FIELD OF THE INVENTION

The present invention relates generally to methods and devices for cardiac surgery, and specifically to methods and apparatus for revascularization, particularly for transmyocardial laser revascularization (TMR).

BACKGROUND OF THE INVENTION

TMR is a technique, known in the art, for creating channels in ischemic heart tissue, typically in the left ventricular wall of the heart, to improve the blood supply to ischemic myocardium. The technique is described, for example, by Mirhosein, et al., in an article entitled "Transmyocardial Laser Revascularization: A Review," in the Journal of Clinical Laser Medicine & Surgery, vol. 11 (1993), pages 15–19, and by Bonn, in an article entitled "High-power lasers help the ischaemic heart," in The Lancet, vol. 348 (1996), page 118, which are incorporated herein by reference.

In TMR, as is known in the art, a computer-controlled laser is used to drill holes about 1 mm in diameter in the myocardium, communicating with the left ventricle, at a typical density of about one hole per square centimeter. Typically, the laser beam is delivered to the epicardium through an incision in the chest and the pericardium that exposes the beating heart. The laser, typically a $CO_2$ laser or, alternatively, an excimer or Ho:YAG laser, fires pulses of about 1000W, which photovaporize the myocardium and create channels through the endocardium into the ventricle. Blood at the outer, epicardial openings of the channels typically clots after a few minutes, but the inner portions of the channels, communicating with the ventricle, remain patent. It is hypothesized that during systole, blood flows through these channels into naturally-existing myocardial sinusoids, supplementing the impaired arterial blood supply.

Particularly when a $CO_2$ laser is used, the laser is generally synchronized to the patient's ECG, so as to fire its pulse during systole, in the refractory period of the heart cycle. Firing the laser pulse at other points in the heart cycle can cause undesirable arrhythmias. The heart rate, myocardial thickness and other factors are used to determine the optimum energy level for each laser pulse.

U.S. Pat. Nos. 5,380,316 and 5,554,152, to Aita, et al., which are incorporated herein by reference, describe methods for intra-operative myocardial revascularization using an elongated, flexible lasing apparatus, which is inserted into the chest cavity of the patient. The distal end of the apparatus is directed to an area of the exterior wall of the heart adjacent to a ventricle and irradiates the wall with laser energy to form a channel through the myocardium.

U.S. Pat. No. 5,389,096, to Aita, et al., which is also incorporated herein by reference, describes methods and apparatus for percutaneous myocardial revascularization (PMR). A deflectable, elongated lasing apparatus is guided to an area within the patient's heart, and the distal end of the apparatus is directed to an area of interest in the inner wall of the heart. The wall is irradiated with laser energy to form channels therein, preferably without perforating the epicardium.

Since in PMR the channels are drilled from the inside of the heart outwards, there is no need for the channels to penetrate all the way through the heart wall, unlike more common TMR methods, in which the channels are drilled from the outside in. In other respects, however, the effects of PMR on the heart are substantially similar to those of TMR. Therefore, in the context of the present patent application, the term TMR will be used to refer to both extracardial and intracardial methods of laser revascularization of the myocardium.

SUMMARY OF THE INVENTION

It is an object of the present invention to provide improved methods and apparatus for TMR.

It is a further object of some aspects of the present invention to provide improved control over the TMR laser drilling procedure, and specifically to control the depth and direction of drilling.

In accordance with some aspects of the present invention, holes are drilled into the myocardium at controlled, substantially predetermined angles. Preferably, the holes are drilled at oblique angles, so as to produce longer channels through the tissue. These longer channels communicate with a greater volume of the myocardium than do channels drilled at approximately right angles to the heart wall, as are known in the art. The oblique channels thereby enhance the perfusion of ventricular blood in the tissue, and may communicate with greater numbers of myocardial sinusoids than do right-angle channels.

It is still another object of some aspects of the present invention to provide methods for mapping and sensing physiological signals in the heart tissue, to be used in conjunction with TMR to adapt and optimize the drilling procedure for the local conditions prevalent in the drilling area in the heart under treatment.

In preferred embodiments of the present invention, a catheter for use in TMR treatment comprises an optical or infrared waveguide and at least one sensor, adjacent the catheter's distal end. The catheter has a distal end, which is surgically inserted into the body and brought into engagement with a surface of the heart muscle, and a proximal end, which is coupled to a console outside the body. The waveguide, preferably an infrared optical fiber, as is known in the art, receives a beam from a high-power laser preferably a pulsed $CO_2$ laser, Ho:YAG or excimer laser, as are known in the art, at the proximal end of the catheter, and directs it at the heart surface. The console receives and analyzes signals from the sensor, in order to guide and control the treatment.

In some preferred embodiments of the present invention, the catheter is inserted into a chamber of the heart, preferably into the left ventricle, by passing the catheter percutaneously through the arterial system. Alternatively, the catheter may be passed through the venous system into the right atrium and ventricle. In these preferred embodiments, the catheter engages the endocardium, and the laser is fired to drill holes into the myocardium from the inside. Preferably, these holes are drilled only to a limited depth, without penetrating the epicardium. Further preferably, the holes are drilled to a depth that is generally sufficient to communicate with the myocardial sinusoids, preferably no more than 8 mm deep, measured in a direction perpendicular to the surface of the heart tissue. More preferably the holes are drilled to a depth of no more than 6 mm, and most preferably, to a depth of about 3 mm.

In other preferred embodiments of the present invention, the catheter is inserted through a surgical incision in the chest wall and then through the pericardium. The catheter engages the epicardium of the left ventricle, and the laser is fired to drill holes through the myocardium and into the left ventricle, guided by the signals received from the sensor at the catheter's distal end.

Preferably, the holes drilled in the heart tissue are approximately one millimeter in diameter. In some preferred embodiments of the present invention, the holes have elliptical, rather than circular cross-section. The elliptical holes have a greater surface area than circular holes of the same cross-sectional area, and therefore may be more effective in enhancing the perfusion of blood into the myocardium. Preferably, the waveguide is flared at the distal end of the catheter to provide an output laser beam profile having a shape and diameter substantially similar to the desired shape and diameter of the holes to be drilled.

In some preferred embodiments of the present invention, the laser is focused onto the heart tissue at a sufficiently high power density to generate shock waves in the tissue. For $CO_2$ laser irradiation, the power density is preferably at least 1 $MW/cm^2$. The shock waves cooperate with the photo-vaporization effect of the laser beam incident on the tissue to drill holes in the myocardium which, it is believed, are more effective in improving perfusion of the myocardium than holes drilled by photovaporization (or ablation) alone. Preferably, at least a portion of the distal end of the catheter, adjacent to the waveguide, is shaped to focus and concentrate shock waves generated by the laser beam into the heart tissue.

In some preferred embodiments of the present invention, the catheter includes a surgical cutting instrument at its distal end. The cutting instrument is used to make an incision, of a controlled, limited depth, through the outer tough layer of the heart tissue, i.e., in the endocardium in embodiments in which the catheter is inserted into the ventricle, or in the epicardium in embodiments in which the catheter is inserted through the chest wall and pericardium. The laser is then fired through the incision in the outer tough layer to drill a hole through the softer inner layers of myocardium. In consequence, a substantially lower-energy laser pulse can be used to produce a hole of desired depth.

Preferably, in these preferred embodiments, the optical waveguide in the catheter is retracted inside the catheter while the cutting instrument makes its incision, and is then extended distally out of the catheter to deliver laser energy into the incision. In this manner, the laser pulse is delivered with greater precision to the desired location in the myocardium.

In some preferred embodiments of the present invention, the catheter is controlled so as to direct the laser beam into the myocardium at a predetermined angle. In contrast to these preferred embodiments, in catheter-based methods and systems known in the art, it is generally not possible to substantially control the beam angle.

In these preferred embodiments, the laser beam is preferably directed obliquely, i.e., at a high angle of incidence with the surface of the heart (measured relative to a direction perpendicular to the surface). Preferably, the angle of incidence is greater than 20°, more preferably greater than 40°, and most preferably greater than 60°. The high angle of incidence of the laser beam causes a hole to be drilled at a correspondingly high angle. The resulting channel through which ventricular blood will flow into the myocardium will generally be longer and is therefore likely to communicate with greater numbers of sinusoids than would a channel at or near normal incidence, as is known in the art. The angle of incidence of the laser beam upon the surface of the heart is most easily and accurately controlled when the catheter is inserted through the chest wall and pericardium and engages the epicardium.

In some of these preferred embodiments, the catheter is configured such that the laser beam is directed out of the distal end thereof in a predetermined oblique angular direction relative to the long axis of the catheter. Optical techniques and devices for such oblique beam delivery are known in the art. When the distal end of such a catheter is brought into engagement with the surface of the heart tissue in a direction substantially perpendicular thereto, for example, the laser beam will be directed into the tissue substantially at the predetermined oblique angle.

Alternatively, a distal portion of the catheter, including the distal end thereof, may be positioned against the heart wall in a substantially tangential position relative thereto. The laser beam is directed obliquely out of the distal end into the heart tissue, substantially as described above. Methods and devices for positioning the catheter in a desired position and orientation in such tangential contact with the heart tissue are described in a U.S. provisional patent application entitled "Conformal Catheter," filed Jan. 3, 1997, which is assigned to the assignee of the present patent application and whose disclosure is incorporated herein by reference. Alternatively or additionally, the catheter may be positioned with the assistance of imaging techniques, such as fluoroscopy, or a position sensor fixed in the catheter, as are known in the art.

In some preferred embodiments of the present invention, the catheter includes a lumen for vacuum suction, which is coupled to a vacuum pump or other suitable suction device, as is known in the art, at the proximal end of the catheter. The suction lumen has an outlet at the distal end of the catheter, which is preferably immediately adjacent to the waveguide. After the distal end is properly positioned in contact with the heart tissue at a point into which a hole is to be drilled, the pump or suction device is activated. A partial vacuum is thus created at the distal outlet of the lumen, which holds the distal end in place while the laser is fired.

Additionally or alternatively, the lumen may be used for passing surgical tools, such as J-shaped retractable barbs, grasping tools and screws, to the outlet at the distal end of the catheter. These tools may be used for performing surgical procedures in the heart, in conjunction with the TMR operation.

In some preferred embodiments of the present invention, the at least one sensor at the distal end of the catheter comprises a position and/or orientation sensor. Preferably, this sensor comprises a plurality of non-concentric coils, which generate signals responsive to an externally-applied, time-varying, magnetic field, as described in PCT patent publication number WO96/05768, filed Jan. 24, 1995, and incorporated herein by reference. Alternatively, the position sensor may comprise a single coil, as described in U.S. Pat. No. 5,391,199, which is also incorporated herein by reference, or several such coils. The coil signals are analyzed to determine position and/or orientation coordinates of the catheter, preferably six-dimensional position and orientation coordinates, as described in the above mentioned PCT publication.

Further alternatively, the position sensor may comprise any suitable type of miniature position and/or orientation sensor known in the art, such as RF sensors, DC magnetic field-responsive sensors, ultrasound sensors, or a Carto system, available from Biosense, Ltd., Tirat Hacarmel, Israel.

The coordinates of the catheter that are derived from the position sensor are used to ascertain that the distal end of the catheter engages the heart tissue at a desired, preferably predetermined position and/or orientation before the laser is fired. Preferably, the coordinates are registered with a map of the heart acquired, for example, by ultrasound imaging. Alternatively, the map may be acquired using a mapping catheter, such as are described in U.S. patent application Ser. No. 08/595,365 and in PCT patent application US95/01103, which are assigned to the assignee of the present patent application, and whose disclosure is incorporated herein by reference.

Preferably, a second, reference catheter, which includes a position sensor of the same or a similar type to that of the TMR catheter described above, is inserted into the heart at a fixed, known position relative thereto. Position and/or orientation coordinates of this reference catheter are used to transform the coordinates of the TMR catheter to a frame of reference that is fixed to the heart. In this way, errors in positioning the TMR catheter that may result from movement of the heart are reduced.

Alternatively, a reference element, including a position sensor, may be placed on the surface of the body and used to transform the coordinates of the TMR catheter to a frame of reference that is fixed to the body. Errors in positioning the TMR catheter due to movement of the body are thus reduced, without the need for the second catheter in the heart, although errors due to movement of the heart cannot be corrected in this fashion.

In some of these preferred embodiments, signals received from the position sensor are used to gate the operation of the laser, as described, for example, in U.S. provisional patent application 60/011,720, which is assigned to the assignee of the present patent application, and whose disclosure in incorporated herein by reference. The laser is allowed to fire only when it is determined that the distal end of the catheter is in the proper position and orientation to drill a desired hole in the heart tissue.

Preferably, the console is pre-programmed with position and orientation coordinates of a plurality of such holes. The catheter is moved over the surface of the heart tissue, and the laser is gated to fire whenever the catheter reaches the coordinates of one of the holes. After a hole is drilled, its position is preferably marked, for example, in computer memory, on a map of the heart, as described above.

In some preferred embodiments of the present invention, the at least one sensor at the distal end of the catheter comprises an electrode, which senses and generates signals responsive to local electrical potentials in the heart tissue. Preferably, signals received from the electrode are used to trigger the firing of the laser pulse, so that the pulse is fired during the appropriate portion of the systolic, refractory period of the tissue that the catheter is engaging. In this manner, local variations in electrical activation and contraction of the heart muscle can be taken into account, to fire the laser at the optimal moment, with greater precision than is possible when the eternally-measured ECG signal is used for this purpose, as is known in the art.

In some of these preferred embodiments, the electrode is used to generate a viability map of the heart, as described in the above-mentioned U.S. patent application Ser. No. 08/595,365, and in U.S. provisional patent application No. 60/009,769, which is assigned to the assignee of the present patent application, and whose disclosure is incorporated herein by reference. Alternatively, the viability map may be generated using a different catheter inside the heart, which is then preferably removed before inserting the TMR catheter.

The viability map is used to identify areas of the heart tissue that are ischemic but still viable, as against other areas that either have adequate perfusion or that have lost their viability due to infarction or prolonged ischemia. The map is preferably based on electrophysiological data, indicative of the flow of activation signals through the heart tissue. Alternatively, the map may be derived from biomechanical data, such as variations in the thickness of the heart wall between systolic and diastolic stages of the heart cycle, or from a combination of biomechanical and electrophysiological data. Preferably, the TMR treatment is performed in the ischemic but still viable areas.

In some preferred embodiments of the present invention, the at least one sensor at the distal end of the catheter comprises an ultrasound transducer. Preferably, the transducer generates signals responsive to the thickness of the heart tissue adjacent to the position of the distal end of the catheter. The thickness-responsive signals are preferably used in determining a desired depth to which the holes in the myocardium are to be drilled. The laser beam energy is then controlled so as to produce holes of this predetermined depth.

Further preferably, signals generated by the transducer are used to monitor the depths and/or directions of holes drilled by the laser.

Additionally or alternatively, the ultrasound signals are used to monitor the thickness of the heart tissue dynamically. As is known in the art, the tissue cyclically thickens during systole and thins during diastole. The laser is triggered so as to fire pulses while the heart tissue is, preferably, substantially at the thickest point in the cycle or, alternatively, at the thinnest point in the cycle. Such thickness-triggered drilling can take the place of laser triggering based on ECG or other electrophysiological signals, potentially enhancing the accuracy and safety of the operation.

Alternatively, in preferred embodiments of the present invention wherein the catheter includes a position and/or orientation sensor adjacent to its distal end, signals received from this sensor may be used to detect movement of the heart wall. The laser is then triggered in response to the rapid, contractile movement of systole.

To summarize, in preferred embodiments of the present invention, the catheter includes laser beam delivery optics and one or more of a variety of sensors, as described above. The one or more sensors preferably include at least one of the following types of sensors, singly or in combination: electrophysiological sensing electrodes; position sensors; ultrasound transducers; other sensors for measuring heart wall thickness, as are known in the art; other sensors for measuring heart tissue viability, as described in the above-mentioned U.S. patent application Ser. No. 08/595,365 or U.S. provisional patent application No. 60/009,769, or otherwise known in the art; and other sensors, known in the art, for measuring perfusion of the heart tissue.

In some preferred embodiments of the invention, the system is triggered in response to other characteristics. For example, the radiation may be triggered in response to one or more of the phase of heart cycle or local mechanical characteristics of the of the heart such as: the velocity of the sensor or its acceleration.

Alternatively or additionally, in some preferred embodiments of the invention, the system is inhibited until a stability condition is met. For example, the radiation may be inhibited unless one or more of the heart cycle, heart rhythm, stability of the position of the distal end of the probe on the heart tissue, stability of the cyclical angular relationship between the distal end of the probe and the heart tissue, stability of the contact between the probe and the tissue.

Some of these conditions may be determined from measurements external to the heart and all of them can be made based on measurements made on the heart itself.

In some preferred embodiments of the present invention, as described above, such catheters are inserted percutaneously and are used to drill channels in the heart tissue endocardially, i.e., from inside a chamber of the heart into the myocardium. In other preferred embodiments, such catheters are inserted through the chest wall and drill channels epicardially, through the myocardium and into a chamber of the heart.

Although in the preferred embodiments described above, the catheter includes a sensor at its distal end, it will be appreciated that some of the methods of the present invention may be applied to perform TMR with greater effectiveness or safety, even without the use of the sensor. For example, in accordance with the principles of the present invention, any suitable laser may be used to drill oblique channels in the myocardium from inside or outside the heart. In this case, the catheter is preferably positioned to drill channels based on a viability map, produced in advance of the TMR procedure.

It should be understood that while the invention is described herein in the context of TMR as defined herein and in particular to the drilling of holes using laser light, its application is broader and includes the control of irradiation of the heart in general and in particular to the formation of one or more irradiation paths within the myocardium by laser light or by other forms of irradiation.

Furthermore, it should be understood that the term "coordinate" as used herein means any of the six coordinates of position and orientation, e.g., the three position and the three orientation coordinates.

There is thus provided in accordance with a preferred embodiment of the invention, an elongate probe for providing irradiation treatment of the heart, said probe having a distal end for engaging heart tissue of a subject, comprising:
  a waveguide, which conveys radiation to the heart tissue for irradiation thereof; and
  a sensor, adjacent the distal end of the probe, which generates signals for use in controlling the treatment.

Preferably, the probe has a longitudinal lumen, which communicates with an orifice in a vicinity of the distal end of the probe. Preferably, the lumen is coupled proximally to a suction device, so as to create a partial vacuum at the orifice. In one preferred embodiment of the invention a surgical cutting instrument is passed through the lumen to the distal end of the probe.

In a preferred embodiment of the invention, the waveguide is extendible distally out of the distal end of the probe.

In a preferred embodiment of the invention the distal end of the probe comprises a generally concave outer surface, for focusing shock waves distal to the distal end, in a vicinity of the waveguide. Preferably, the concave outer surface comprises a fiberoptic faceplate formed at the distal end of the waveguide.

In a preferred embodiment of the invention, the probe further comprises a focusing lens, which focuses the radiation along an axis related to the probe. Preferably, the lens focuses the radiation such that the radiation forms a beam having a generally elliptical profile.

In a preferred embodiment of the invention, the radiation is directed out of the probe at a predetermined oblique angle relative to the long axis of the probe. Preferably, the probe comprises an optical deflection element, which directs the radiation out of the probe at the oblique angle.

Preferably the sensor comprises at least one electrode, which receives electrophysiological signals from the heart tissue.

Alternatively or additionally the sensor comprises an ultrasound transducer. Preferably, the ultrasound transducer emits a steerable ultrasound beam in a generally distal direction relative to the distal end of the probe.

Alternatively or additionally the sensor comprises a coordinate sensor. Preferably the coordinate sensor generates signals indicative of six-dimensional position and orientation coordinates of the probe, the coordinate sensor comprises one or more coils, which generate signals responsive to an externally-applied magnetic field.

There is further provided, in accordance with a preferred embodiment of the invention, apparatus for treatment of the heart, comprising:
  a probe according as described above;
  a radiation source, coupled to the waveguide in the probe; and
  a control unit, comprising an irradiation actuator, which receives the signals from the sensor in the probe and controls the source responsive to the signals.

Preferably the apparatus comprises a positioning actuator which steers the distal end of the probe so as to irradiate the heart tissue at a desired coordinate.

In a preferred embodiment of the invention the apparatus comprises:
  a control unit including a positioning actuator, which receives the signals from the coordinate sensor in the probe and controls the coordinates of the distal end of the probe responsive to the signals.

Preferably, the control unit determines position coordinates of the distal end of the probe based on the signals and the positioning actuator steers the probe based on the position coordinates so as to engage the heart tissue in a desired position.

Preferably, the control unit determines orientation coordinates of the distal end of the probe based on the signals and the positioning actuator steers the probe based on the orientation coordinates so as to engage the heart tissue at a desired angle. Preferably, the control unit compares the coordinates to a predetermined value and triggers the radiation source only when the coordinates are substantially equal to the predetermined value.

In a preferred embodiment of the invention the apparatus comprises according to any of claims 18–23, and comprising a reference probe, wherein the control unit determines coordinates of the reference probe and refers the coordinates of the probe to the coordinates of the reference probe. Preferably, the control unit controls the probe based on the coordinates so as to irradiate the tissue at a desired angle.

There is further provided in accordance with a preferred embodiment of the invention apparatus for treatment of the heart, comprising:
  an elongate probe having a distal end for engaging heart tissue of a subject, and comprising a waveguide, which conveys radiation to the heart tissue for treatment thereof;
  a source of radiation, coupled to the waveguide in the probe; and
  a control unit comprising a positioning actuator which controls the coordinates of the probe so as to irradiate the surface at a controllable angle.

Preferably, the probe also comprises a sensor adjacent its distal end, wherein said sensor supplies signals to the control unit.

In a preferred embodiment of the invention the control unit triggers the radiation source responsive to variations in the signals.

Preferably, the control unit controls the radiation source to drill channels to a desired depth. Preferably, the control unit determines the depth of the channels, based on the signals, so as to control the radiation source to drill channels to a desired depth.

In a preferred embodiment of the invention, the control unit triggers the radiation source responsive to variations in the signals. Preferably, the control unit triggers the radiation source responsive to the phase of the heart cycle.

In a preferred embodiment of the invention the control unit triggers the radiation source based on a local mechanical characteristic of the heart. Preferably the local mechanical characteristic includes one or more of a position of a sensor coupled to a portion of the to the heart; a velocity of a sensor coupled to a portion of the heart; an acceleration of a sensor coupled to a portion of the heart; and an orientation of a sensor with respect to a portion of the heart.

In a preferred embodiment of the invention, the control unit triggers the radiation source only when a stability condition is met. Preferably, the stability condition includes one or more of stability of the heart cycle to within a given stability; stability of the heart rhythm to within a given stability; stability of the position of the distal end of the probe on the tissue to within a given stability; stability of the cyclical angular relationship between the distal end of the probe and the tissue to within a given stability; and stable contact between the probe and the tissue.

The stability condition may be derived from a measurement made external to or internal to a patient being treated, as appropriate.

In a preferred embodiment of the invention the probe includes a lumen and the apparatus includes a source of irrigating liquid which supplies said liquid for irrigating the tissue.

In a preferred embodiment of the invention the radiation source is a laser.

There is further provided, in accordance with a preferred embodiment of the invention, apparatus for treatment of the heart comprising:

means for applying a treatment at successive positions on the heart; and a memory in which the successive positions are stored.

In a preferred embodiment of the invention the means for applying includes a probe; and the apparatus comprises: a display which displays a map of the heart; and a controller which marks the display of the heart with a treatment position when a treatment is applied.

In a preferred embodiment of the invention, the display indicates the position of each of the successive treatments.

Preferably, the treatment comprises irradiation of the heart with a radiation source. Preferably the radiation source is a laser. Alternatively or additionally the treatment comprises the formation of irradiation paths within the myocardium. Alternatively or additionally the treatment comprises drilling of holes in the myocardium.

There is further provided, in accordance with a preferred embodiment of the invention, a method for treatment of the heart, comprising:

bringing a probe into engagement with a surface of the heart tissue of a subject; and irradiating the heart tissue via the probe at a controllable angle, which may be an oblique angle, relative to the surface, which may be either the epicardium or the endocardium of the heart.

In preferred embodiments of the invention the angle is at least 20°, 40° or 60° relative to an axis perpendicular to the surface.

In a preferred embodiment of the invention irradiating comprises generating shock waves in the heart tissue, preferably, concentrating the shock waves in the heart tissue by reflection of the waves from a concave surface of the probe.

There is further provided, in accordance with a preferred embodiment of the invention a method for heart treatment, comprising:

bringing a probe, into engagement with a surface of the heart tissue of a subject;

irradiating the tissue with radiation via the probe, wherein the radiation generates shock waves in the heart tissue; and concentrating the shock waves in the heart tissue by reflection of the waves from a concave surface of the probe.

In preferred embodiments of the invention irradiation includes photovaporizing the tissue. Alternatively or additionally the irradiation is laser radiation.

Preferably, irradiation comprises forming a plurality of irradiation paths in the tissue. In a preferred embodiment of the invention the paths have a generally elliptical cross-section.

There is further provided, in accordance with a preferred embodiment of the invention a method of treatment of the heart, comprising:

bringing a probe into engagement with a surface of the heart tissue of a subject;

forming one or more irradiation paths having an elliptical cross-section in the heart tissue by irradiating the heart via the probe.

Preferably the irradiation is laser irradiation. Alternatively or additionally, forming an irradiation path comprises drilling a channel. In a preferred embodiment of the invention the method comprises drilling the channels to a depth of no more than 10 mm, measured in a direction perpendicular to the surface of the endocardium. More preferably the depth is not more than 6 or approximately 4 mm.

In a preferred embodiment of the invention bringing the probe into engagement with the surface of the heart tissue comprises bringing a distal portion of the probe into tangential contact with the heart tissue, and wherein irradiating the heart tissue comprises directing radiation from the probe at an angle relative to a long axis of the probe.

Preferably, the method includes exerting suction through a lumen in the probe so as to anchor the probe to the tissue in a desired position.

In a preferred embodiment of the invention the method comprises controlling the irradiation responsive to the characteristic that is sensed.

There is further provided, in accordance with a preferred embodiment of the invention, a method for treatment of the heart, comprising:

bringing a probe, into engagement with a surface of the heart tissue of a subject;

sensing a local characteristic of the heart; and irradiating the heart via the probe, while controlling the irradiation responsive to the characteristic that is sensed.

Preferably, sensing the characteristic of the heart comprises sensing electrical potentials in the heart tissue.

Preferably, controlling the irradiation responsive to the characteristic comprises triggering the irradiation responsive to the potentials.

In a preferred embodiment of the invention sensing the characteristic of the heart comprises producing a viability map of the heart and/or receiving ultrasound signals from the tissue and/or analyzing the ultrasound signals to determine the thickness of the heart tissue in a vicinity of the probe. Preferably, controlling the irradiation responsive to the characteristic comprises triggering the irradiation responsive to variations in the thickness. Preferably, sensing the characteristic of the heart tissue comprises analyzing the ultrasound signals to determine the depth of the channels.

Preferably, controlling the irradiation responsive to the characteristics comprises controlling the irradiation to drill channels having a desired depth.

In a preferred embodiment of the invention the method comprises receiving and analyzing signals from a coordinate sensor coupled to the probe to determine coordinates of the probe, wherein bringing the probe into engagement with the surface of the heart tissue comprises controlling the coordinates of engagement of the probe based on the coordinates.

There is further provided, in accordance with a preferred embodiment of the invention a method for treatment of the heart, comprising:

receiving and analyzing signals from a coordinate sensor coupled to a probe to determine coordinates of the probe;

bringing the probe into engagement with a surface of the heart tissue of a subject, while controlling the coordinates of engagement of the probe based on the signals; and forming one or more irradiation paths in the heart tissue by irradiating the heart tissue with radiation via a waveguide in the probe.

Preferably, receiving and analyzing the signals to determine the coordinates of the probe comprises determining six-dimensional position and orientation coordinates of the probe.

Preferably controlling the coordinates of engagement of the probe comprises controlling the probe's angular orientation relative to the surface of the heart tissue.

Preferably, receiving and analyzing the signals from the coordinate sensor comprises receiving and analyzing signals generated in response to a magnetic field applied to the probe.

In a preferred embodiment of the invention the method comprises registering the coordinates of the probe with a map of the heart. Preferably, registering the coordinates with the map of the heart comprises registering the coordinates with a viability map of the heart.

In a preferred embodiment of the invention, the method comprises recording the coordinates of the one or more irradiation locations relative to the map of the heart.

In a preferred embodiment of the invention the method comprises selecting probe target coordinates corresponding to at least one of the irradiation paths to be formed in the heart tissue, wherein forming the paths comprises triggering the irradiation when the coordinates of the probe correspond to the target coordinates of the at least one of the channels.

Preferably forming irradiation paths comprises triggering the irradiation responsive to a change in the signals received from the coordinate sensor indicative of systolic contraction of the heart.

Preferably the method further comprises:

fixing a reference probe to the heart; and receiving and analyzing signals from the reference probe to determine coordinates thereof, wherein receiving and analyzing the signals from the position sensor coupled to the probe to determine the coordinates of the probe comprises referring the coordinates of the probe to the coordinates of the reference probe.

The present invention will be more fully understood from the following detailed description of the preferred embodiments thereof, taken together with the drawings in which:

DETAILED DESCRIPTION OF PREFERRED EMBODIMENTS

Figure 1A:
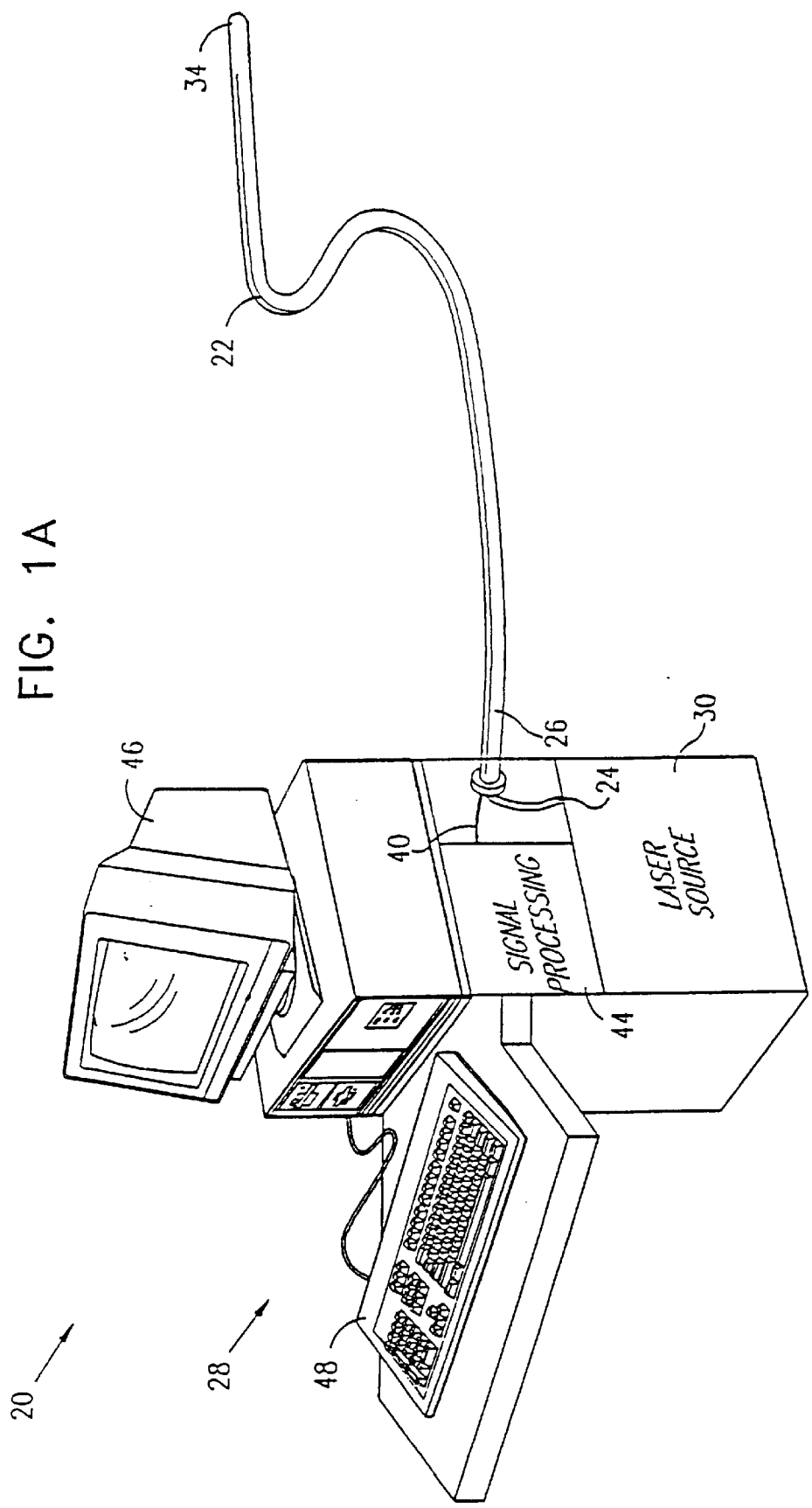
FIG. 1A is a schematic illustration of a catheter system for use in irradiation treatment such as TMR, in accordance with a preferred embodiment of the present invention.
Figure 1B:
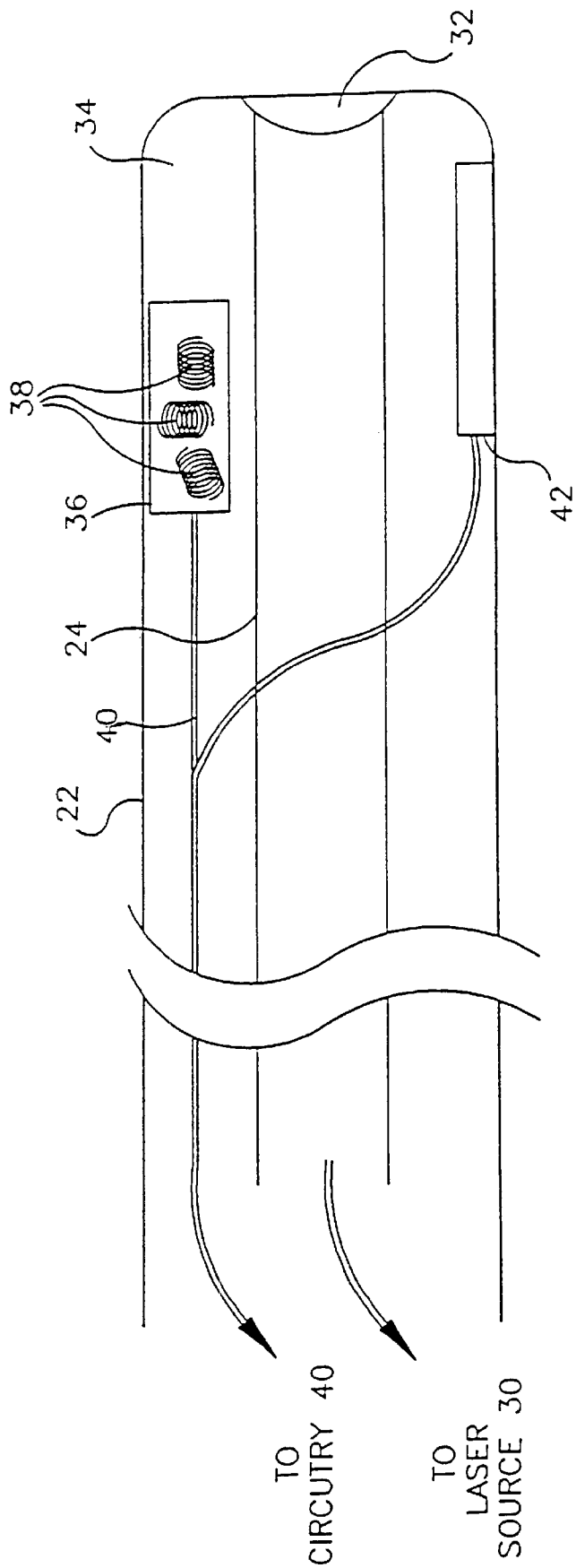
FIG. 1B is a schematic illustration showing details of the distal end of the catheter of FIG. 1A, in accordance with a preferred embodiment of the present invention.

Reference is now made to FIGS. 1A and 1B, which schematically illustrate a system 20 for TMR, including a catheter 22 for insertion into the body of a subject, in accordance with a preferred embodiment of the present invention. Catheter 22 comprises an optical waveguide 24, preferably an infrared-transmitting optical fiber or a hollow waveguide tube, suitable for transmitting $CO_2$ laser radiation, as is known in the art. Alternatively, waveguide 24 may be of a type, likewise known in the art, that transmits visible, near-infrared or near-ultraviolet wavelengths. Preferably, a focusing lens 32 at distal end 34 of catheter 22, as is known in the art, focuses the laser radiation from waveguide 24 into heart tissue, as will be described below.

Catheter 22 is connected at its proximal end 26 to a console 28, which includes a laser source 30 optically coupled to waveguide 24. Source 30 preferably comprises a $CO_2$ laser, or alternatively, a Ho:YAG or excimer laser, but it will be clear to those skilled in the art that other types of pulsed, high-power lasers may similarly be used, with appropriate changes to the waveguide and other elements of system 20. Preferably, console 28 also includes signal processing circuitry 44, as well as a display 46 and user controls 48 comprised in a control unit. In general, the control unit performs sensing calculating and other functions of the system which are described below.

Catheter 22 further includes a position sensor 36, fixed in a known position adjacent distal end 34. Preferably, sensor 36 comprises three miniature non-concentric coils 38, as described in the above-mentioned PCT publication WO 96/05768, although alternatively, other types of position sensors may similarly be used. Coils 38 generate electrical signals responsive to a magnetic field applied by field generators coils (not shown in the figures) outside the body. These signals are conveyed via wires 40 in catheter 22 to circuitry 44, which analyzes them to determine six-dimensional position and orientation coordinates of distal end 34. These coordinates are used in positioning catheter 22 prior to drilling holes in the myocardium, as will be described below. In some preferred embodiments of the invention fewer than six coordinates, for example, only one or two orientation coordinates, are required as will be clear from the context of the embodiments.

As shown in FIG. 1B, catheter 22 preferably also includes an electrode 42 at its distal end, for sensing electrical potentials in heart tissue adjacent to distal end 34. Local electrogram signals from electrode 42 are similarly conveyed by wires 40 to circuitry 44. Preferably, these signals are used to trigger laser source 30, most preferably during the refractory portion of the electrogram waveform.

In one preferred embodiment of the present invention, heart 50 is artificially paced. This pacing is particularly important in cases of pre-existing cardiac rhythm disorders. The pacing may be provided by external pacing or by inserting an additional pacing catheter, as is known in the art. Alternatively, pacing pulses may be applied to electrode 42, or a separate pacing electrode may be added to catheter 22.

Although catheter system 20 is shown and described with reference to certain types of sensors, it will be understood that catheter 22 may include other sensors and other types of elements, as are known in the art. For example, additional electrodes may be placed at or adjacent to distal end 34, either on catheter 22 itself or on a structure fixed to the catheter, as described in U.S. provisional patent application No. 60/011,724, filed Feb. 15, 1996, which is assigned to the assignee of the present patent application, and whose disclosure is incorporated herein by reference. These multiple electrodes may be used, for example, to measure electrical conduction velocity in the heart tissue adjacent to catheter 22, and TMR treatment, as will be described below, is preferably concentrated at sites of low conduction velocity.

Sensor 36 may further comprise any suitable miniature position sensor known in the art, such as other types of magnetic field-responsive sensors or ultrasonic position sensors. Preferably, catheter 22 also includes a deflection mechanism, as is known in the art (but for simplicity not shown in the figures), for steering distal end 34. For example, catheter 22 may include a two-radius mechanism, as is known in the art, wherein the catheter bends in two generally opposite directions, with a different radius of curvature in each of the two directions. A preferred apparatus for deflection of the distal end of a catheter is described in a PCT Patent Application entitled "MAPPING CATHETER" whose disclosure is incorporated herein by reference and which is filed on even date with and assigned to the same assignee as the present application.

Figure 2A:
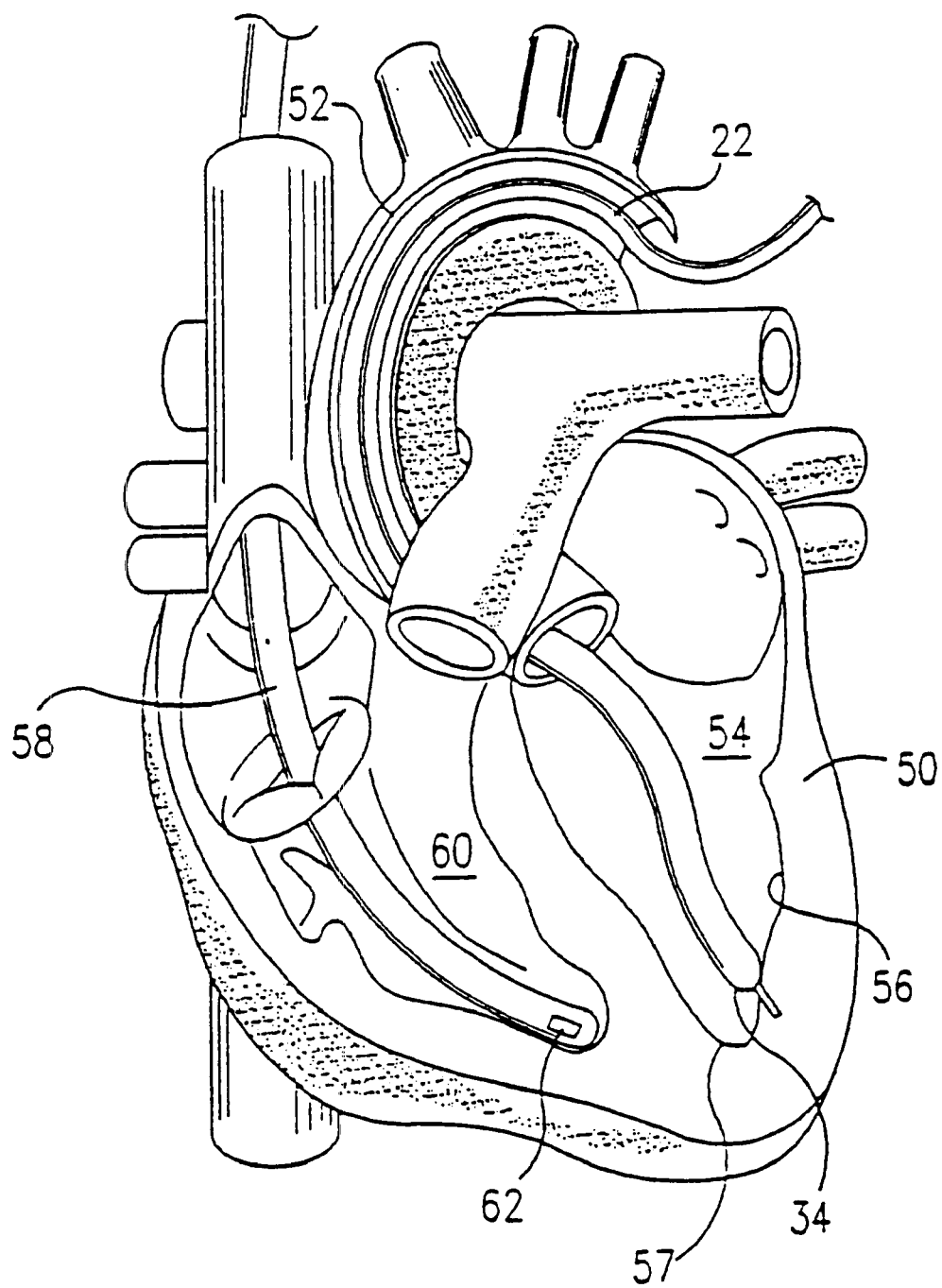
FIG. 2A is a schematic, sectional illustration of a human heart, into which the catheter of FIGS. 1A and 1B is inserted for performing irradiation treatment such as a TMR procedure therein, in accordance with a preferred embodiment of the present invention.

FIG. 2A is a schematic, sectional illustration showing catheter 22 inserted into heart 50 of a subject, in accordance with a preferred embodiment of the present invention. Catheter 22 is fed percutaneously into the subject's vascular system, for example, through the femoral artery, and is passed through aorta 52 into left ventricle 54 of heart 50. Distal end 34 is positioned against endocardium 56 in a desired position and orientation and drills holes therein, as will be described below.

As shown in FIG. 2A, preferably, a second, reference catheter 58 is also inserted through the vasculature and fixed in place in the heart 50, for example, in right ventricle 60, or in one of the coronary arteries. Reference catheter 58 includes a position sensor 62, preferably of the same type as sensor 36. The position of catheter 58 in heart 50 is preferably verified using methods of cardiac imaging, such as X-ray, CT or ultrasound imaging. In this way, the position and/or orientation coordinates of catheter 58 that are determined from signals generated by sensor 62 may be registered with the shape and features of the heart. These coordinates are used to establish a frame of reference that is fixed to heart 50, to which the coordinates of the distal end of catheter 22 are referred.

Alternatively, a reference element (not shown in the figures) including position sensor 62 may be fixed to the outside of the subject's body. In this case, the coordinates of the reference element, determined from signals generated by sensor 62, are used to establish a frame of reference that is fixed to the body, to which the coordinates of the distal end of catheter 22 are referred. Preferably, sensor 62 is gated to operate in synchronism with the subject's breathing and/or heart beat.

Further alternatively or additionally, the coordinates of sensor 36 may be registered with a geometric map of the heart, for example, as produced in accordance with the above-mentioned U.S. patent application Ser. No. 08/595,365, or with a viability map of the heart, as described below. Such viability maps may be produced by the apparatus and method described in detail in a PCT Application of even date entitled "CARDIAC ELECTROMECHANICS," which is assigned to the assignee of the present invention and whose disclosure is incorporated herein by reference.

Figure 2B:
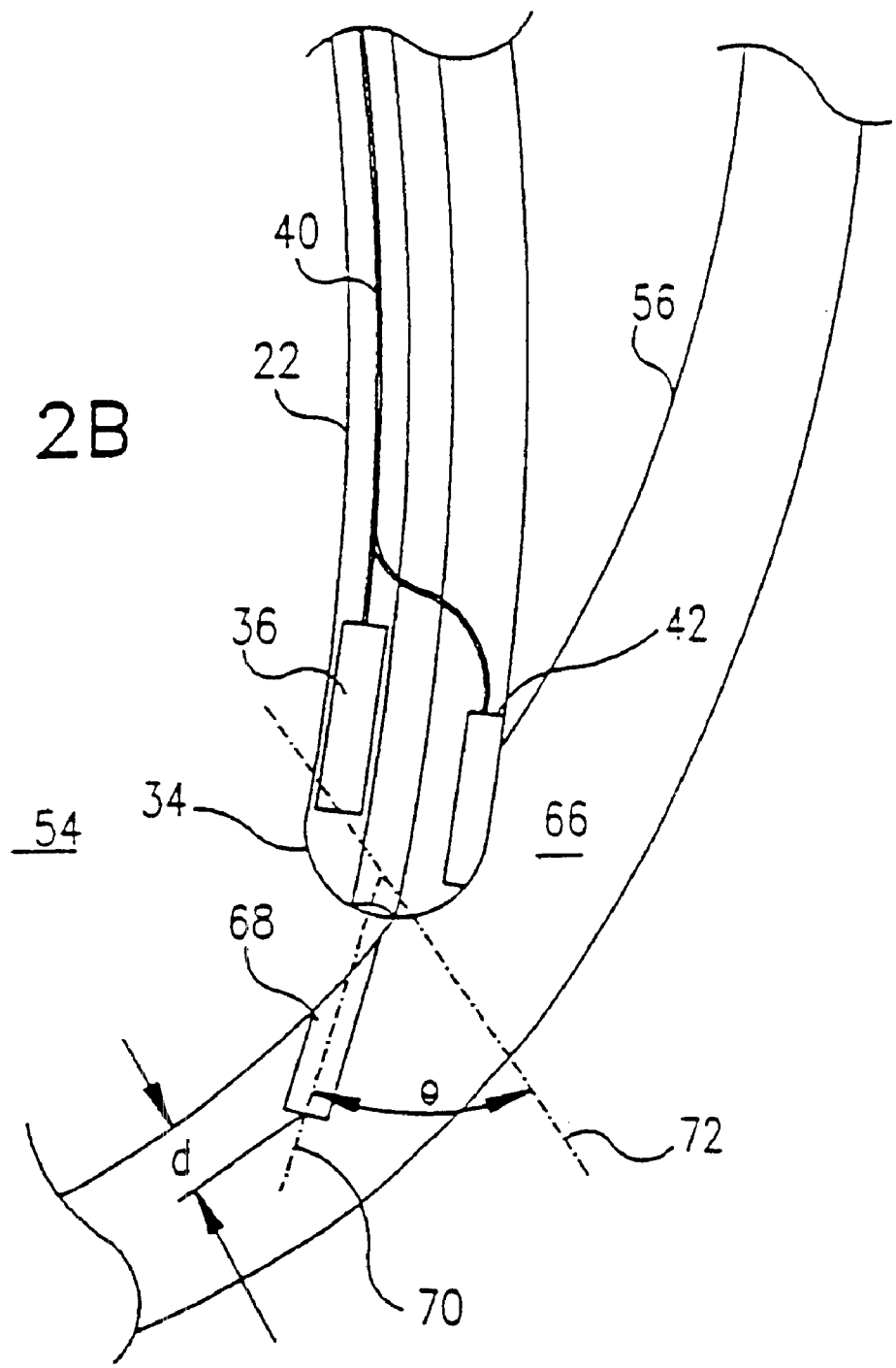
FIG. 2B is a schematic, sectional detail illustration showing a channel drilled in the tissue of the heart of FIG. 2A, in accordance with a preferred embodiment of the present invention.

FIG. 2B is a schematic, sectional illustration showing details of catheter 22 drilling a channel 68 in myocardium 66 of heart 50, in accordance with a preferred embodiment of the present invention. Distal end 34 of catheter 22 preferably engages endocardium 56 at an oblique angle θ, defined as the angle between optical axis 70 of lens 32 and an axis 72 perpendicular to the surface of endocardium 56. As a result, channel 68 is drilled through endocardium 56 to a desired depth d within myocardium 66, at the oblique angle θ. Preferably, d is less than or equal to 8 mm, as against methods of TMR known in the art, in which channels are drilled all the way through myocardium 66, or at least to a depth of 10–30 mm therein. More preferably, d is less than or equal to 6 mm, and most preferably, it is approximately equal to 3 mm.

The use of catheter 22 to create such shallow, oblique channels as channel 68 permits blood from ventricle 54 to reach a relatively large number of sinusoids within myocardium 66, while limiting unneeded damage to the heart tissue. Furthermore, the shallow, oblique channels are more effective in supplying blood to the inner portion of myocardium 66, nearest to ventricle 54, which portion tends to suffer most severely from ischemia.

Preferably, holes 68 drilled in the heart tissue are approximately one millimeter in diameter. In some preferred embodiments of the present invention, holes 68 are drilled with elliptical, rather than circular cross-section. The elliptical holes have a greater surface area than circular holes of the same cross-sectional area, and therefore may be more effective in enhancing the perfusion of blood into myocardium 66. Preferably, waveguide 24 is flared at the distal end of the catheter to provide an output laser beam profile having a shape and diameter substantially similar to the desired shape and diameter of the holes to be drilled. Additionally or alternatively, lens 32 may comprise an angularly non-uniform focusing element, known in the art, for example, a cylindrical lens, for creating the desired non-circular beam profile.

In some preferred embodiments of the present invention, the laser beam is focused onto the heart tissue at a sufficiently high power density to generate shock waves in the tissue. When laser source 30 comprises a $CO_2$ laser, the power density is preferably at least 1 MW/cm$^2$. The shock waves cooperate with the ablative effect of the laser beam incident on the tissue to drill channels 68 in myocardium 66 which, it is believed, are more effective in improving perfusion of the myocardium than holes drilled by ablation alone.

Figure 3A:
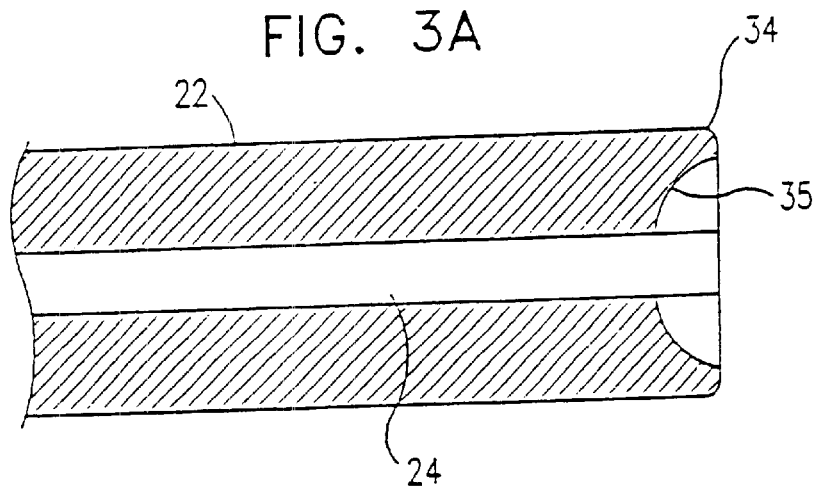
FIGS. 3A, 3B and 3C are schematic, sectional illustrations showing details of the distal ends of catheters for use in irradiation treatment such as TMR, in accordance with alternative preferred embodiments of the present invention.

Thus, FIG. 3A is a schematic, sectional illustration of distal end 34 of catheter 22 in accordance with an alternative preferred embodiment of the present invention, in which a portion of the distal end of the catheter, adjacent to waveguide 24, is shaped to form a concave reflective surface 35. This surface focuses and concentrates shock waves generated by the laser beam, incident on the heart issue, so as to increase the effectiveness of channels 68 drilled thereby.

Figure 3B:
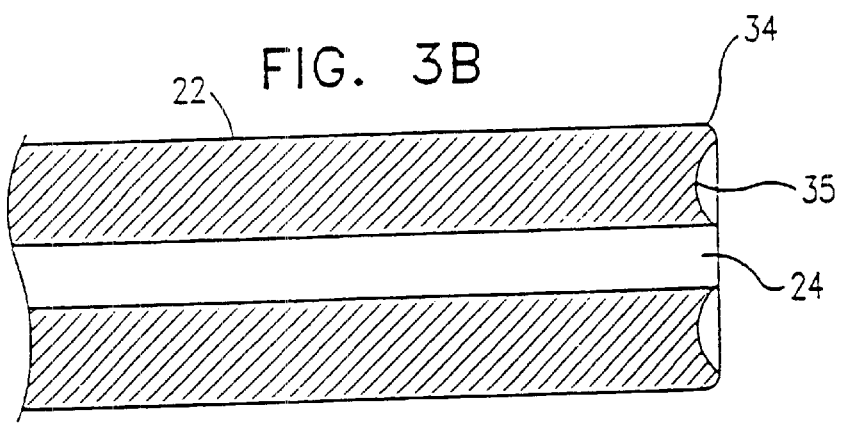

FIG. 3B is a schematic, sectional illustration of distal end 34 in accordance with another, similar preferred embodiment of the present invention. In this case, waveguide 24 does not protrude substantially beyond reflective surface 35, as in FIG. 3A, but is, rather, generally flush with the surface. The shape of distal end 34 of catheter 22 shown in FIG. 3B may be less prone to damage of waveguide 24 and to capture of foreign matter, such as blood clots, within the area of surface 24 than that shown in FIG. 3A.

It will be understood that the configurations of waveguide 24 and surface 35 or faceplate 38 in FIGS. 3A and 3B are shown by way of illustration, and other configurations may similarly be used to achieve the desired effect of focusing shock waves into the heart tissue. The end of the waveguide may be either flush with or protrude from the surface and may be either centered, as shown in the figures, or off-center with respect to distal end 34 of catheter 22. Furthermore, the optical fibers need not pass through the entire length of catheter 22 in a single bundle, as shown in FIGS. 3A and 3B, but may rather be distributed radially within the catheter and then brought together at distal end 34.

Figure 3C:
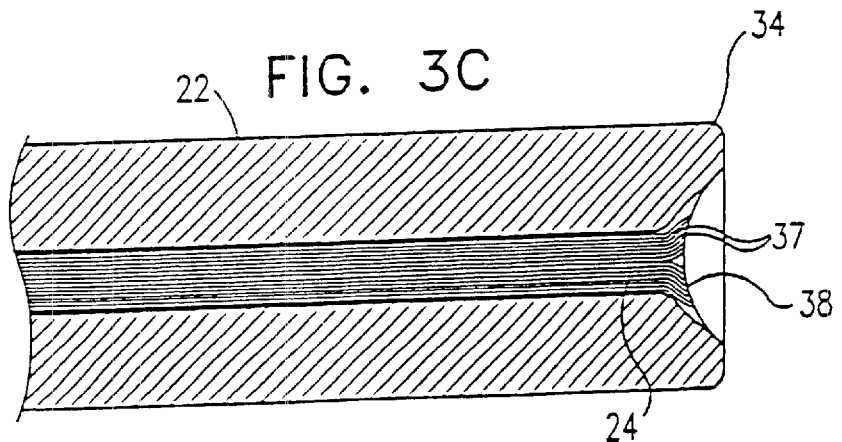

FIG. 3C is a schematic, sectional illustration of distal end 34 in accordance with still another preferred embodiment of the present invention, useful particularly when laser source 30 comprises a Ho:YAG or other near infrared laser. Waveguide 24 shown in FIG. 3C preferably comprises a bundle of optical fibers 37, which are fused and flared, as is known in the art, at distal end 34 to form a concave faceplate 38. Alternatively, the waveguide may comprise a single fiber, whose distal end is ground and polished to form a concave structure similar to faceplate 38. Like reflective surface 35 described above, faceplate 38 focuses and concentrates the laser-generated shock waves.

Referring again to FIG. 2B, the position and orientation coordinates determined with respect to sensor 36 are used to ascertain that distal end 34 of catheter 22 is properly positioned before drilling channel 68. Preferably, signals generated by sensor 36 are used to gate laser source 30, so that the source will fire only when distal end 34 is properly positioned and oriented. Alternatively, the signals generated by sensor 36 may be used to gate a shutter (not shown in the figures), which interrupts the laser beam and prevents its reaching waveguide 24, except when distal end 34 is properly positioned and oriented. Further preferably, console 28 is pre-programmed with position and orientation coordinates corresponding to a plurality of channels, like channel 68. As distal end 34 is moved over myocardium 66 in ventricle 54, source 30 is gated to fire whenever the distal end reaches the proper, pre-programmed position and orientation coordinates for drilling one of the channels. After each channel is drilled, its position is preferably recorded by console 28 and may be marked on a map of the heart, as described herein.

As shown in FIG. 2B, electrode 42 is brought into contact with endocardium 56, so as to receive electrogram signals from the heart tissue. Preferably, before laser source 30 is fired, electrode 42 is used to generate a viability map of heart 50, as described in the above-mentioned U.S. patent applications Ser. No. 08/595,365 and No. 60/009,769. This map may be produced from inside the heart, as shown here, or alternatively from the outside of the heart, as illustrated, for example, in FIG. 4B. To produce the map, electrode 42 is moved along endocardium 56 in a generally spiral pattern, preferably beginning at apex 57 and moving up toward aorta 52. The viability map is used to identify areas of myocardium 66 that are ischemic but still viable, as against other areas that either have adequate perfusion or that have lost their viability due to infarction or prolonged ischemia. Such ischemic areas are characterized by some or all of the following characteristics: (1) little or no response to activation signals; (2) little or no diastolic expansion and/or systolic contraction; (3) slow conduction velocity; (4) low electrogram signal levels; and (5) presence of injury currents.

Preferably, the TMR treatment is performed in the ischemic but still viable areas. Further preferably, the treatment is performed immediately following infarction, to relieve ischemia and prevent further damage to the heart tissue.

Figure 4A:
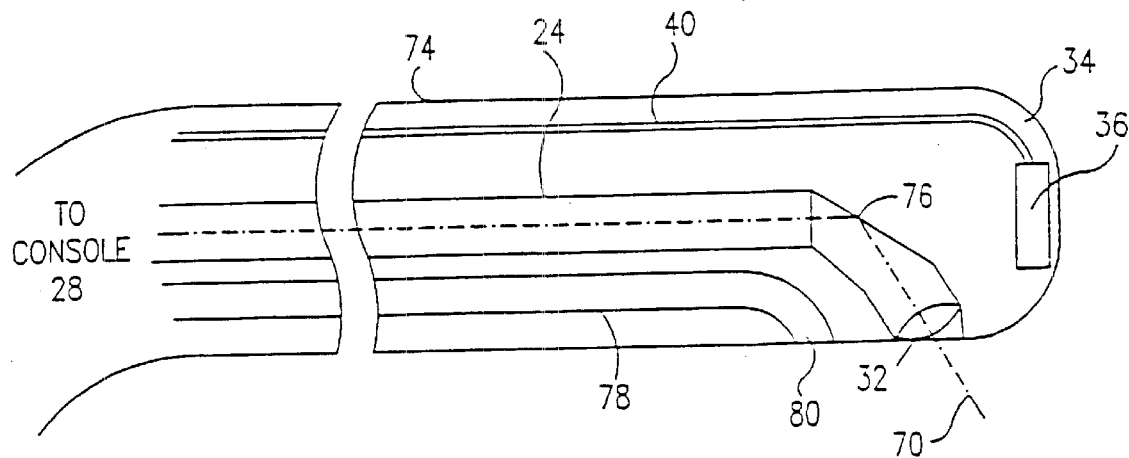
FIG. 4A is a schematic illustration showing details of the distal end of another catheter for use in irradiation treatment such as TMR, in accordance with a preferred embodiment of the present invention.

FIG. 4A is a schematic illustration showing details of distal end 34 of a side-firing catheter 74, which is substituted for catheter 22 in accordance with an alternative preferred embodiment of the present invention. Catheter 74 includes position sensor 36 and waveguide 24, which are coupled at the catheter's proximal end (not shown in the figure) to console 28, in a manner substantially similar to that described above with reference to catheter 22. In catheter 74, however, an optical deflection element 76, as is known in the art, deflects the beam of laser energy transmitted through waveguide 24, so that the beam is emitted from distal end 34 along axis 70 at a predetermined oblique angle.

Catheter 74 preferably also includes a lumen 78, preferably serving as a suction channel, which terminates in an orifice 80 at or near distal end 34. Lumem 78 is coupled to a suitable pump or other suction device, as is known in the art, in console 28. Lumen 78 may also be used for other purposes, such as for flushing or irrigating the distal end of waveguide 24 and/or heart tissue adjacent thereto and/or for passing a miniature surgical device (shown below in FIG. 4C) through to orifice 80.

Catheter 74 may preferably include one or more electrodes, like electrode 42 in catheter 22, and a deflection mechanism for steering the catheter, as described above. These elements are not shown in FIG. 4A for the sake of simplicity.

Figure 4B:
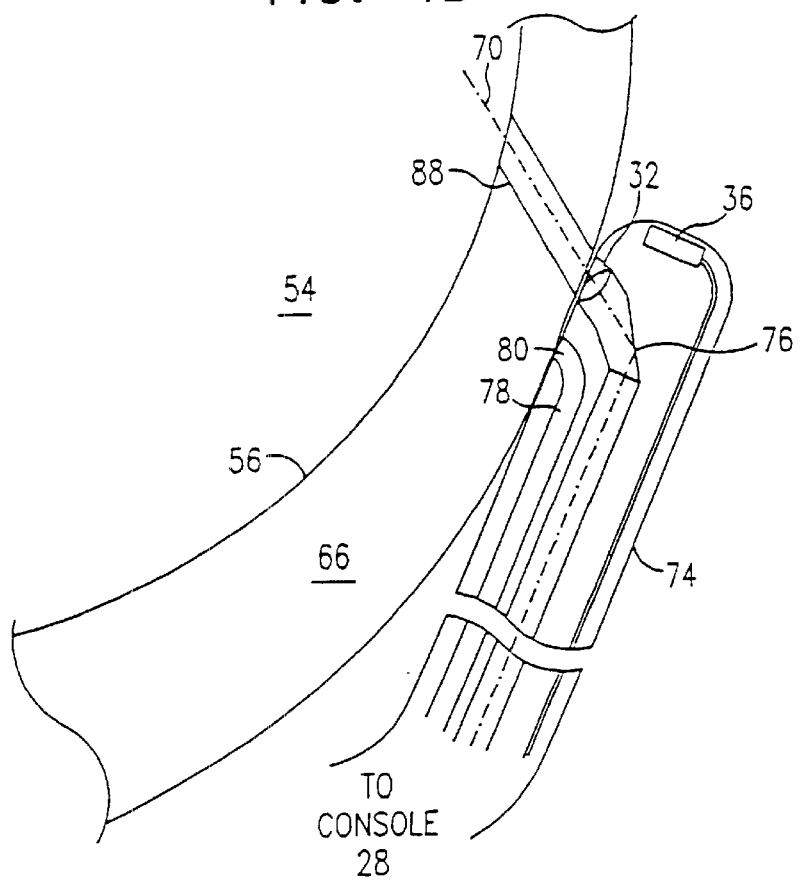
FIG. 4B is a schematic, sectional detail illustration of a human heart, against whose outer surface the catheter of FIG. 4A is brought into engagement for performing irradiation as for example in a TMR procedure, in accordance with another preferred embodiment of the present invention.
Figure 4C:
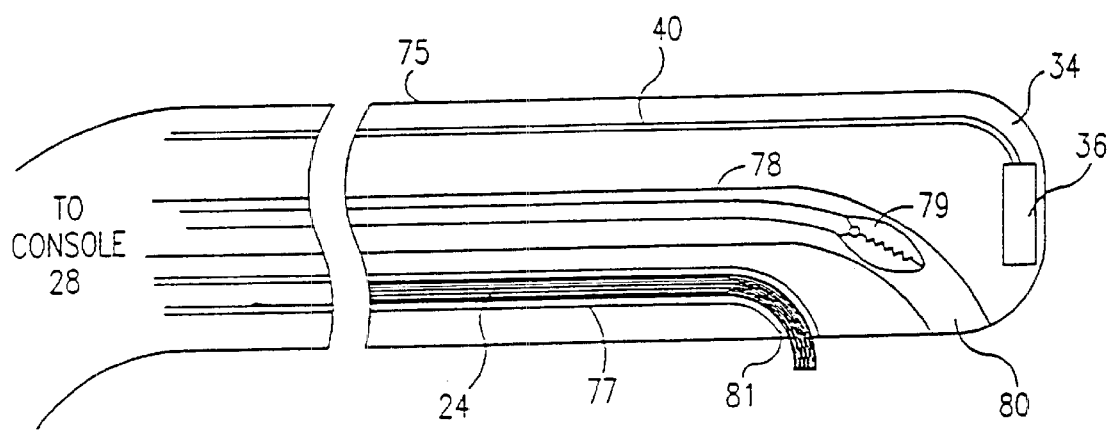
FIG. 4C is a schematic illustration showing details of the distal end of still another catheter for use in irradiation treatment such as TMR, in accordance with a preferred embodiment of the present invention.

FIG. 4B is a schematic, sectional illustration showing a detail of heart 50, in which catheter 74 drills an oblique TMR channel 88, in accordance with a preferred embodiment of the present invention. In this embodiment, catheter 74 is inserted through incisions in the chest wall and in the pericardium of the subject, as is known in the art, preferably minimally-invasive incisions 1–2 cm wide, and is brought into engagement with epicardium 82. A portion of catheter 74 adjacent to and including distal end 34 is placed tangentially along the surface of the epicardium at a desired position. Preferably, lumen 78 is suctioned so as to create a partial vacuum at orifice 80, thereby anchoring distal end 34 in position. Alternatively, a surgical device may be passed through lumen 78 (as shown in FIG. 4C, for example) and used to anchor catheter 74 mechanically by grasping epicardium 82, instead of using suction for this purpose. Laser source 30 is activated, so that channel 88 is drilled through myocardium 66 and endocardium 56 into ventricle 54, in the desired position and at the predetermined angle.

Position readings of sensor 36 may be used to produce a geometrical map of the outer surface of heart 50. These readings may be registered with another geometrical map 777 of the inner surface of the heart, produced as described in the above-mentioned U.S. patent application Ser. No. 08/595,365, for example. The outer and inner maps are then compared to determine the thickness of the heart tissue at the location of catheter 74. If catheter 74 includes a suitable electrode, as described above, electrical activity on the outer surface of heart 50 may also be mapped.

It will be understood that catheter 74 may be used in a similar manner to drill channels, like channel 68 shown in FIG. 2B, from the inside of ventricle 54. In this case, the distal portion of the catheter is preferably positioned tangentially against endocardium 56. Preferably, the position of catheter 74 is registered with topographical features of ventricle 54, for example, as described in the above-mentioned provisional application of Jan. 3, 1997.

Whether catheter 74 operates from inside or outside of heart 50, it will be appreciated that the tangential placement of catheter 74, particularly when used in conjunction with suction through orifice 80, ensures that the catheter will remain stable while channels 68 or 88 are drilled. On account of this tangential positioning, the channels are formed at the desired angle, as determined by optical deflection element 76.

FIG. 4C is a schematic illustration showing details of distal end 34 of a side-firing catheter 75, which is substituted for catheter 74, in accordance with another preferred embodiment of the present invention. Catheter 75 includes a surgical cutting instrument 79, contained within lumen 78. Instrument 79 is extended out through opening 80 to make a small incision in the tough, outer layer of the heart tissue, through which incision the laser beam is fired to create a channel in softer myocardium 66.

Optical waveguide 24 in catheter 75 preferably comprises a flexible fiberoptic bundle, contained within an additional lumen 77 of the catheter. Preferably, waveguide 24 is retracted inside the catheter while the cutting instrument makes its incision, and is then extended distally out of the catheter through an opening 81 to deliver laser energy into the incision. In this manner, the laser pulse is delivered with greater precision to the desired location in the myocardium.

Figure 5:
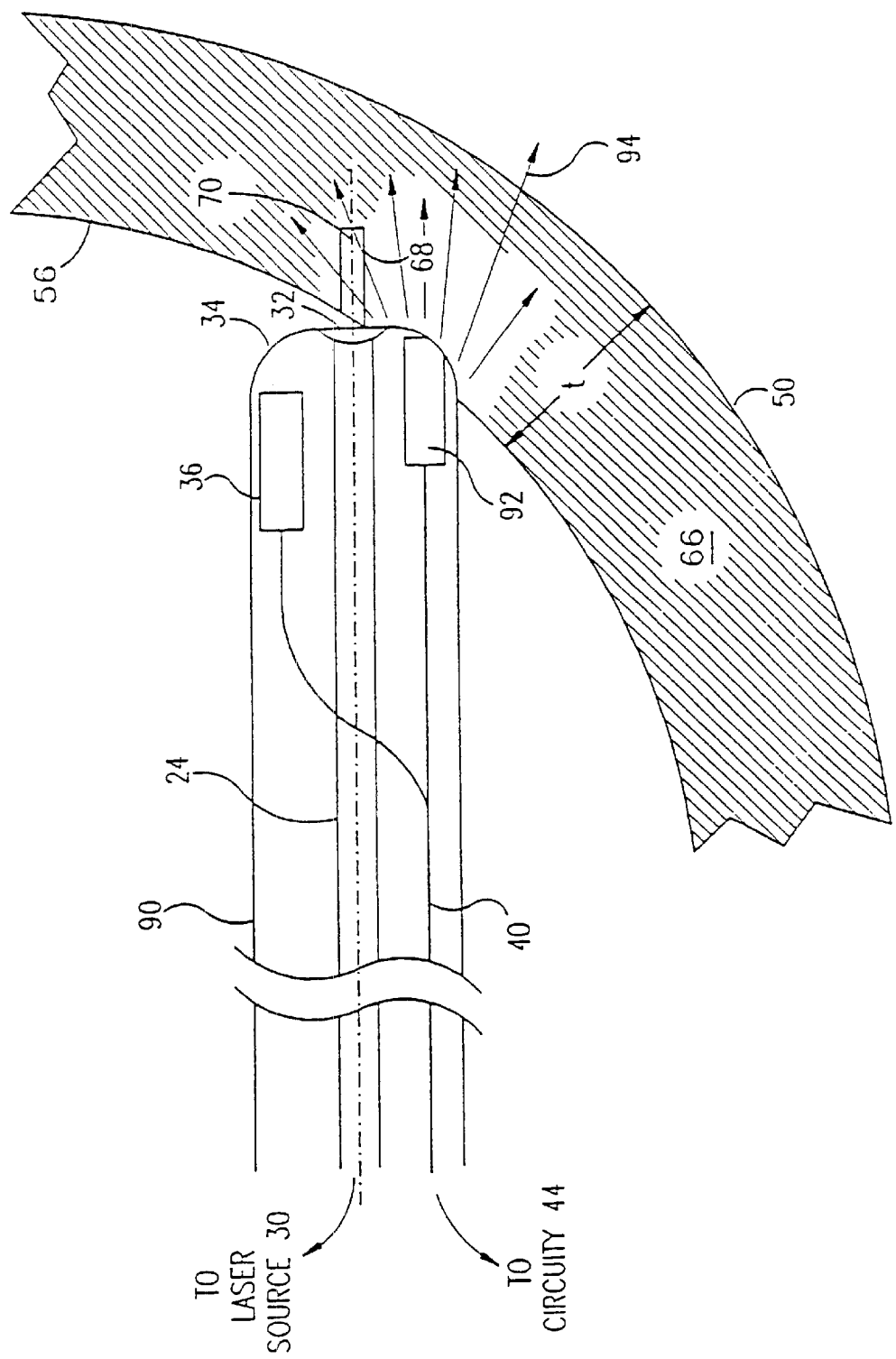
FIG. 5 is a schematic illustration showing details of the distal end of yet another catheter for use in irradiation treatment such as TMR, in contact with the tissue of a human heart, in accordance with an alternative preferred embodiment of the present invention.

FIG. 5 is a schematic illustration showing details of another catheter 90 for use in TMR, in accordance with a preferred embodiment of the present invention. Catheter 90 includes waveguide 24, lens 32 and position sensor 36, and is coupled to console 28, substantially as described above with reference to catheter 20. Additionally, catheter 90 includes an ultrasound transducer 92. Preferably, transducer 92 comprises a transducer array, as is known in the art, which emits a beam 94 that may be steered over a range of angles distal to distal end 34 of catheter 90. Alternatively, for monitoring the thickness of the heart wall, as will be described below, a single transducer element may similarly be used. Transducer 92 is coupled via wires 40 to signal processing circuitry 44.

Catheter 90 is preferably brought into oblique contact with the tissue of heart 50, for example, with endocardium 56, as shown in FIG. 5. Signals received by circuitry 44 from transducer 92 are used to measure a thickness, t, of the wall of heart 50. The measured thickness is preferably used in determining an optimal depth to which channel 68 should be drilled, so that laser source 30 may be controlled accordingly. Further preferably, following each pulse or several pulses of the laser source, the transducer signals are used to measure the depth and direction of channel 68 and determine whether the optimal, desired depth has been reached and whether catheter 90 is properly aimed.

Additionally, transducer 92 is preferably used to monitor wall thickness t dynamically, making multiple measurements over the course of each heart cycle. Preferably, this dynamic measurement is used to trigger laser source 30, so that the source is fired during the local systolic contraction, when the wall of heart 50 is at or near its greatest thickness. This thickness-based triggering may be used in conjunction with or in place of triggering based on electrophysiological signals, as described above.

Although in the embodiments described above, catheters 22, 74 and 90 include various sensors and optical elements in certain preferred combinations and configurations, it will be appreciated that in other preferred embodiments of the present invention, TMR catheters may include some or all of these sensors and elements in other combinations and in the same or other configurations. Such catheters may also include other types of sensors known in the art, for example, temperature or pressure sensors, useful in diagnosing other aspects of cardiac function.

Figure 6:
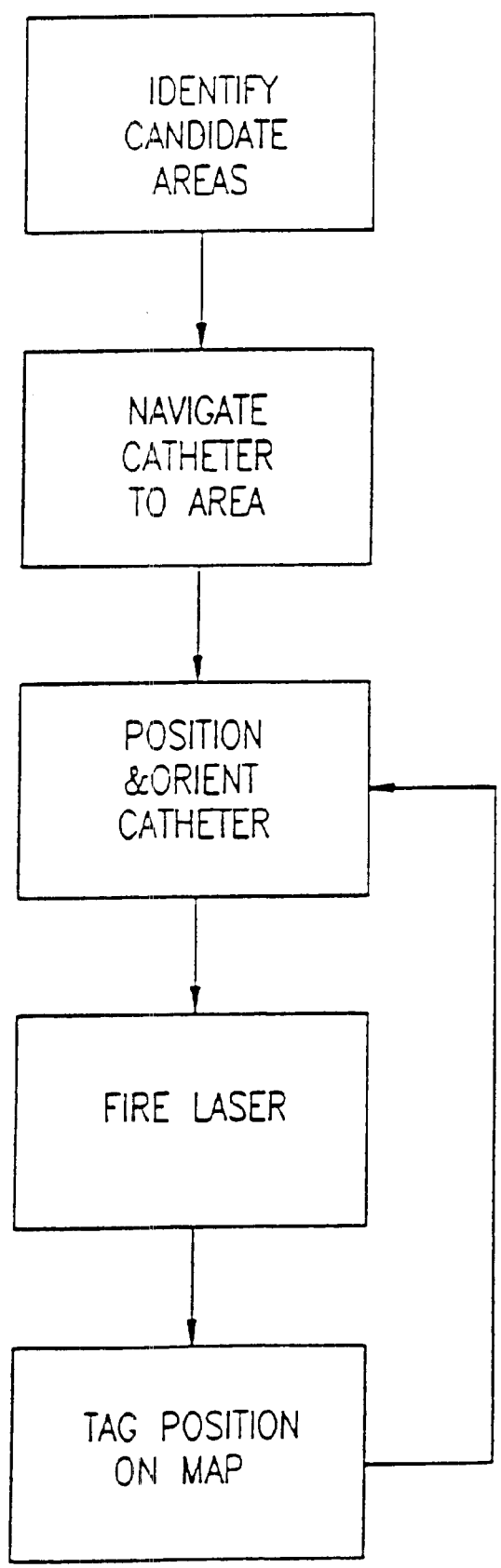
FIG. 6 is a flow chart illustrating a procedure for irradiation treatment such as TMR, in accordance with a preferred embodiment of the present invention.

FIG. 6 is a flow chart that summarizes the key steps in a method for TMR, in accordance with preferred embodiments of the present invention. The method is described below with reference to catheter 22, shown in FIGS. 1A and 1B, but it will be understood that the principles of this method may be applied using other suitable catheters, as described hereinabove.

Prior to beginning TMR, at least one candidate area for the procedure is identified within heart 50. The area may be identified by means of viability mapping or measurement and mapping of the thickness of the heart wall, as described above, or by other methods known in the art, such as a NOGA, available from Biosense, Ltd., Tirat Hacarmel, Israel. Preferably, borders of the candidate area are marked on a map of the heart, stored by console 28.

Catheter 22 is then navigated to the candidate area. The position and orientation of distal end 34 of the catheter are ascertained and controlled by a positioning actuator in the control unit based on signals received from position sensor 36, and are compared with the stored map of the heart. Alternatively, the position actuator may be operated by an operator based on the received signals or displays and maps containing information derived from the signals.

When the distal end is suitably positioned and oriented, laser source 30 is fired, for example by a irradiation actuator to drill a channel in the heart tissue, as described above. The position of the channel is marked on the map, and catheter 22 is then repositioned to drill the next channel. This procedure is preferably repeated until channels have been drilled to a desired density over the entire candidate area.

It will be appreciated that the principles and methods of the present invention may be applied using catheters and apparatus of other types known in the art, for example, to drill narrow, shallow channels 68. These channels may be drilled using a laser source, as described above, or alternatively, using drills of other suitable types known in the art, for example, a high-speed roto-ablator drill head. Alternatively, the channels may be produced using a focused, high-intensity beam of ultrasonic radiation. In this case, preferably, before firing the ultrasonic beam, microbubbles are injected into the heart tissue at the site of a channel to be drilled, as described in Israel patent application no. 119,137, which is assigned to the assignee of the present patent application and incorporated herein by reference. Although in the preferred embodiments described above, catheters 22, 74 and 90 are used to drill channels in the wall of left ventricle 54, it will be understood that similar devices and techniques, in accordance with the principles of the present invention, may be used to drill holes in other chambers of heart 50.

In some preferred embodiments of the invention, the system is triggered in response to other characteristics. For example, the radiation may be triggered in response to one or more of the phase of heart cycle or local mechanical characteristics of the of the heart such as: the velocity of the sensor or its acceleration.

Alternatively or additionally, the radiation may be initiated by based on signals generated by one or more of other sensors such as: electrophysiological sensing electrodes; ultrasound transducers; other sensors for measuring heart wall thickness, as are known in the art; other sensors for measuring heart tissue viability, as described in the above-mentioned U.S. patent application Ser. No. 08/595,365 or U.S. provisional patent application No. 60/009,769, or otherwise known in the art; and other sensors, known in the art, for measuring perfusion of the heart tissue.

Alternatively or additionally, in some preferred embodiments of the invention, the system is inhibited until a stability condition is met. For example, the radiation may be inhibited unless one or more of the heart cycle, heart rhythm, stability of the position of the distal end of the probe on the heart tissue, stability of the cyclical angular relationship between the distal end of the probe and the heart tissue, stability of the contact between the probe and the tissue.

Furthermore while irradiation may be responsive to many inputs, generally irradiation does not occur unless at least some of these inputs are present. For example, in an exemplary system, irradiation is inhibited unless the operator gives a positive command, for example, by depressing a foot-switch.

Some of these conditions may be determined from measurements external to the heart and all of them can be made based on measurements made on the heart itself.

It will be appreciated that the preferred embodiments described above are cited by way of example, and the full scope of the invention is limited only by the claims.

What is claimed is:

1. A system for treatment of a tissue, the system comprising:
    (a) a laser source;
    (b) a catheter having:
        (i) an optical waveguide operatively connected to the laser source;
        (ii) a position sensor for generating position signals relating to a distal end of the catheter;
        (iii) an electrode for generating signals relating to viability of the tissue;
    (c) signal processing circuitry for processing the position signals for determining position coordinates of the distal end of the catheter and the signals relating to viability of the tissue for determining a viability map of the tissue; and
    (d) a display for displaying the viability map.

2. The system according to claim 1, wherein the viability map includes electrophysiological data.

3. The system according to claim 2, wherein the viability map includes biomechanical data.

4. The system according to claim 1, wherein the laser source is pulsed.

5. The system according to claim 4, wherein the laser source is Ho:YAG.

6. The system according to claim 5, wherein the signal processing circuitry also determines orientation coordinates for the distal end of the catheter.

7. The system according to claim 1, wherein the position sensor is a magnetic field-responsive sensor.

8. The system according to claim 7, wherein the position sensor is an ultrasound sensor.

9. The system according to claim 7, further comprising a reference element for establishing a frame of reference for the position sensor.

10. The system according to claim 1, wherein the tissue is in a patient's heart.

* * * * *